US008639343B2

(12) United States Patent
De Vos (10) Patent No.: US 8,639,343 B2
(45) Date of Patent: *Jan. 28, 2014

(54) EAR STIMULATOR FOR PRODUCING A STIMULATION SIGNAL TO AN EAR

(75) Inventor: Gerrit Johannis De Vos, 's-Heerhendrikskinderen (NL)

(73) Assignee: NasoPhlex B.V. (NL)

( * ) Notice: Subject to any disclaimer, the term of this patent is extended or adjusted under 35 U.S.C. 154(b) by 234 days.

This patent is subject to a terminal disclaimer.

(21) Appl. No.: 13/000,008

(22) PCT Filed: Jun. 18, 2009

(86) PCT No.: PCT/NL2009/050358
§ 371 (c)(1), (2), (4) Date: Mar. 14, 2011

(87) PCT Pub. No.: WO2009/154458
PCT Pub. Date: Dec. 23, 2009

(65) Prior Publication Data
US 2011/0166619 A1 Jul. 7, 2011

(30) Foreign Application Priority Data
Jun. 18, 2008 (NL) .................................. 2001694

(51) Int. Cl.
*A61N 1/18* (2006.01)
(52) U.S. Cl.
USPC .................. 607/42; 607/47; 607/48; 600/529
(58) Field of Classification Search
None
See application file for complete search history.

(56) References Cited

U.S. PATENT DOCUMENTS

| 4,969,468 A | 11/1990 | Byers et al. |
| 5,178,156 A * | 1/1993 | Takishima et al. ............ 600/537 |
| 5,335,657 A | 8/1994 | Terry, Jr. et al. |
| 5,514,175 A | 5/1996 | Kim et al. |
| 5,571,148 A | 11/1996 | Loeb et al. |

(Continued)

FOREIGN PATENT DOCUMENTS

| CA | 2507142 | 10/2006 |
| DE | 29716688 | 11/1997 |

(Continued)

OTHER PUBLICATIONS

Benacka et al, "The Sniff-Like Aspiration Reflex Evoked by Electrical Stimulation on the Nasopharynx," Respiration Physiology, pp. 163-174, Dec. 1, 1995.

(Continued)

*Primary Examiner* — Brian T Gedeon
*Assistant Examiner* — Ankit Tejani
(74) *Attorney, Agent, or Firm* — Fliesler Meyer LLP (57) ABSTRACT

An electronic stimulation system to be worn in, behind or on a human ear having a casing; a detection device to sense breathing activity from a human being and to generate a detection signal; electronics within the casing and having a controller connected to the detection device to process the detection signal and generate a control signal when the controller has determined that the human being is in a state of developing apnoea; a stimulation device to receive the control signal from the electronics and to provide stimuli to one or more points of the human ear; wherein when the electronic stimulation system is worn in, behind or on the human ear, the stimulation device is pushed against a predetermined portion of the human ear.

25 Claims, 5 Drawing Sheets

(56) References Cited

U.S. PATENT DOCUMENTS

| | | | |
|---|---|---|---|
| 5,891,185 | A | 4/1999 | Freed et al. |
| 5,957,956 | A | 9/1999 | Kroll et al. |
| 6,368,287 | B1 | 4/2002 | Hadas |
| 6,603,654 | B2 | 8/2003 | Rorvick et al. |
| 6,928,324 | B2 | 8/2005 | Park et al. |
| 6,988,993 | B2 * | 1/2006 | Sullivan et al. ............... 600/528 |
| 2002/0123777 | A1 * | 9/2002 | Dolgin et al. ................... 607/60 |
| 2003/0100930 | A1 | 5/2003 | Cohen et al. |
| 2003/0139781 | A1 | 7/2003 | Bradley et al. |
| 2003/0199945 | A1 | 10/2003 | Ciulla |
| 2004/0176673 | A1 | 9/2004 | Wahlstrand et al. |
| 2004/0210261 | A1 * | 10/2004 | King et al. ......................... 607/9 |
| 2004/0215236 | A1 | 10/2004 | Lattner et al. |
| 2004/0243205 | A1 | 12/2004 | Keravel et al. |
| 2005/0159790 | A1 | 7/2005 | Shalev |
| 2006/0020299 | A1 | 1/2006 | Shalev |
| 2006/0064139 | A1 | 3/2006 | Chung et al. |
| 2006/0149319 | A1 | 7/2006 | Kuo et al. |
| 2006/0173259 | A1 | 8/2006 | Flaherty et al. |
| 2006/0206162 | A1 | 9/2006 | Wahlstrand et al. |
| 2006/0217779 | A1 | 9/2006 | Ransbury et al. |
| 2007/0088404 | A1 | 4/2007 | Wyler et al. |
| 2007/0118011 | A1 * | 5/2007 | Harrison et al. ................ 600/25 |
| 2007/0128420 | A1 | 6/2007 | Maghribi |
| 2007/0255379 | A1 | 11/2007 | Williams et al. |
| 2007/0255531 | A1 | 11/2007 | Drew |
| 2008/0103545 | A1 | 5/2008 | Bolea et al. |
| 2009/0240296 | A1 | 9/2009 | Zeijlemaker et al. |

FOREIGN PATENT DOCUMENTS

| | | |
|---|---|---|
| EP | 0404427 | 12/1990 |
| EP | 1790380 | 5/2007 |
| EP | 1825880 | 8/2007 |
| WO | WO 00/66215 | 11/2000 |
| WO | WO 2004/049937 | 6/2004 |
| WO | 2006079484 A1 | 8/2006 |
| WO | WO 2006/108630 | 10/2006 |
| WO | WO 2007/003019 | 1/2007 |
| WO | WO 2007/146213 | 12/2007 |
| WO | WO 2007/147046 | 12/2007 |
| WO | WO 2008/072948 | 6/2008 |
| WO | WO 2008/080062 | 7/2008 |
| WO | WO 2008/157435 | 12/2008 |

OTHER PUBLICATIONS

Janssens et al., "Respiratory and Cardiac Arrest Under General Anesthesia: Treatment by Acupuncture fo the Nasal Philtrum," Vet. Rec., 105(12), pp. 273-276, Sep. 22, 1979.

Tomori et al., "Hypoxic Apnea Induced by N2 Inhalation Can Be Reversed by the Aspiration Reflex of Anaesthetized Cats," Respiratory Medicine, vol. 85, pp. 61-65, Jan. 1, 1991.

Wang et al., "Clinical Observation on Effect of Auricular Acupoint Pressing in Treating Sleep Apnea Syndrome," Medline, Oct. 23, 2003.

Chang, et al., Decrease of anesthetics activity by electroacupuncture on Jen-Chung point in rabbits, Neuroscience Letters 202, Oct. 2, 1995, pp. 93-96, Elsevier Science Ireland Ltd.

Hsu, et al., Shock resuscitation with acupuncture: case report, Emergency Medical Journal, 2006, 2 pages.

Oleson, et al., Electroacupuncture & auricular electrical stimulation, IEEE Engineering in Medicine and Biology Magazine, Dec. 1983, pp. 22-26.

Tomori, et al., Reflex reversal of apnoeic episodes by electrical stimulation of upper airway in cats, Respiration Physiology, Jul. 3, 1995, pp. 175-185, vol. 102, Elsevier Science B.V.

Tomori, et al., Mechanisms and clinicophysiological implications of the sniff- and gasp-like aspiration reflex, Respiration Physiology, Jul. 27, 1998, vol. 114, Elsevier Science B.V.

Zheng, et al., Mechanisms of effects of electrical stimulation of "Renzhong" (DU 26) on phrenic discharge in rabbits, Dec. 1989, pp. 384-388.

Miller, Oral and pharyngeal reflexes in the mammalian nervous system: their diverse range in complexity and the pivotal role of the tongue, Critical Reviews in Oral Biology & Medicine, Sep. 1, 2002, pp. 409-425, International and American Associations for Dental Research.

* cited by examiner

EAR STIMULATOR FOR PRODUCING A STIMULATION SIGNAL TO AN EAR

PRIORITY CLAIM

This application claims priority to the following foreign patent applications:
International Patent Application No. PCT/NL2009/050358, filed Jun. 18, 2009, by Gerrit Johannis de VOS, entitled EAR STIMULATOR FOR PRODUCING A STIMULATION SIGNAL TO AN EAR; and
Netherlands Patent Application No. 2001694, filed Jun. 18, 2008, by Gerrit Johannis de VOS, entitled EAR STIMULATOR FOR PRODUCING A STIMULATION SIGNAL TO AN EAR, each of which is incorporated herein by reference.

FIELD OF THE INVENTION

The invention relates to an electronic system for producing a stimulation signal to an ear. Such a stimulation signal is chosen such that it will induce an aspiration reflex in human beings.

BACKGROUND OF THE INVENTION

The brainstem contains a number of central mechanisms regulating a number of vital physiological functions. Disorders in the regulation of the cardio-pulmonary system can result in a number of pathological conditions some of which may be potentially life threatening.

People suffering from sleep apnoea have cardio-pulmonary disorders manifesting with breathing irregularities and even frequent stops of breathing (apnoea), particularly during sleep, but also during the day. The apnoeic episodes during the daytime are less dangerous, because they can be self-managed by conscious actions, apnoeas during the night are more dangerous. Patients can feel very sick in everyday life, due to oxygen deprivation. During episodes of apnoea, blood pressure can collapse and subsequently the heart may stop its function, resulting in inadequate brain perfusion, loss of consciousness and even sudden death. At least 4% of the adult population in developed countries suffers from sleep apnoea.

There are several types of apnoea. One type, central apnoea, involves a dysfunction of the respiratory muscles (including the diaphragm) for lack of command from the respiratory centre in the brainstem. This is the type occurring in approximately 10 percent of the cases. Another type, obstructive apnoea, occurs in 80% of cases, when in spite of respiratory movements there is no supply of air to the lungs, due to collapse of the upper airways. The third type, a mixed apnoea, occurs in the rest of the patients.

It is known, that apnoea can be counteracted by stimulation of the patient in various ways. In infants shaking is usually enough to arouse the baby from sleep and restart the process of automatic breathing and even provoke gasps, which induces resuscitation from asphyxia. Adults suffering from sleep apnoea now sleep with a mask, tightly connected to the facial contours, so a slight over-pressure of air from a device can continuously be applied (Continuous Positive Airway Pressure—CPAP). This keeps the airways open and allows air supply by spontaneous breathing. In any case these patients have to sleep attached to their breathing apparatus, limiting their freedom of movement during sleep. For patients with sleep apnoea travelling means carrying the breathing apparatus with them. For patients suffering from central sleep apnoea or mixed type sleep apnoea, treatment with CPAP is showing limited success. Modulating the air pressure (BI-PAP) offers only a slightly better success rate.

Research in cats has shown that breathing can be stopped by inhalation of anoxic mixtures for over 1 minute, with subsequently a severe drop in blood pressure and heart rate. Mechanical or electrical stimulation of the nasopharynx can induce a sniff- and gasp-like "aspiration reflex" (Tomori and Widdicombe, 1969, Beňačka & Tomori, 1995, Tomori et al. 1995, 1998, 2000). Due to resuscitation effects, the blood pressure returns to normal, heart rhythm normalizes, respiration and neuro-behavioral functions return to normal. The anesthetized cat seems to be in good condition, even after as long as three minutes without adequate blood pressure, heart rate and breathing. This experiment can be repeated over 10 times on the same cat, without any noticeable negative consequences.

Provocation of such an aspiration reflex has been indicated as a possible means for interruption of apnoea in cats (Tomori et al., 1991, 1995, Beňačka & Tomori, 1995, Jakus et al., 2004). Alternatively, similar resuscitation may be induced by (electro)-acupuncture, (electro)-acupressure or mechanical stimulation of the nasal philtre in cats, inducing spasmodic inspiration (Beňačka & Tomori, 1997).

International Patent Application No. PCT/NL2006/000599, which has not been published prior to the priority date of the present invention, describes the surprising discovery that a resuscitating stimulation of the brainstem with an induced aspiration reflex in order to obtain resuscitating physiological effects also works in human beings. That document also describes some devices designed for treating apnoea and related cardio-respiratory syndromes in humans via activation of the respiratory centre of the brainstem followed by an induced aspiration reflex.

International Patent Application No. PCT/NL2006/000599 describes an ear stimulator in general terms.

International Publication No. WO2007/147046 discloses an apparatus that can be worn by a user. The apparatus comprises a first portion that can be worn on, behind or in the ear and a second portion that can be attached under a human nose. The second portion comprises a detector to sense a breathing signal of the user. The first portion comprises a stimulation device which is designed to provide a stimulus to the human's acoustic nerve inside the ear when the device detects a disturbance in the respiratory cycle of the user, e.g., caused by sleep apnoea.

International Publication No. WO00/66215 discloses an apparatus comprising a sensor and a stimulation device both connected to a control unit. The control unit is arranged to determine whether or not a user is suffering from a respiratory disorder, such as sleep apnoea, in dependence on signals received from the sensor and to control the stimulation device such as to stimulate nerves in the labyrinth of a human ear to counteract the disorder.

Wang Xiao-hong, et al., Chinese Journal of Integrated Traditional and Western Medicine, October 2003, p. 747-749, disclose some observations on the effect of aurical acupoint pressing in treating sleep apnoea. They report that in the night after acupoint pressure had been applied people showed an improved apnoea-hypopnoea index. They do not disclose any apparatus or method to counteract apnoea at a time it occurs.

SUMMARY OF THE INVENTION

The object of the present invention is to provide an improved ear stimulation device that can be used to generate a stimulus to ears.

To that end, the invention provides an ear stimulator as claimed in claim 1.

The advantage of such a device is that most of its components can be worn inside, behind or on the ear. Advanced devices for wearing inside or outside the ear are available as hearing aids. Starting from such known hearing aid devices, a device can be designed for the present invention.

BRIEF DESCRIPTION OF THE DRAWINGS

The invention will be explained in detail with reference to some drawings that are only intended to show embodiments of the invention and not to limit the scope. The scope of the invention is defined in the annexed claims and by its technical equivalents.

DESCRIPTION OF EMBODIMENTS

The present invention, among others, relates to devices suitable for inducing autoresuscitation in a subject in need thereof. The term autoresuscitation should be understood to comprise resuscitation by activation of natural compensatory mechanisms of the human organism via inducing a sniff- and/or gasp-like aspiration reflex, or its alternative forms in various species, similar to that provided by means of spontaneous gasping autoresuscitation observed in non-human animals and human infants (Sridhar et al., 2003; Xie et al., 2004). When referring to induction of autoresuscitation in this specification the term resuscitation may be used. Subjects that may benefit from induction of autoresuscitation are subjects suffering from and/or having a predisposition for functional disorders, such as hyper and hypo-function of the: a) respiratory system, b) cardiovascular system, c) neurobehavioral changes and d) psychiatric disorders. These include one or more of apnoea, fibrillating heart disorder, transient ischemic attacks (TIA), bronchospasm also in asthmatics, laryngospasm, hiccup, tremor associated with Parkinson's disease, epileptic seizure, absence type epilepsy, migraine, hypotension, syncope, haemorhagic shock (loss of blood), alternating hemiplegia, Alzheimers disease, depression, anorexia nervosa, bulimia, autism, psychiatric disorders, sleep paralysis, insomnia, comatose states.

It is believed that the "aspiration reflex", via strong activation of the inspiratory centre, causes the controlling functions of the brainstem to be reset, similar to activation of brainstem centres during autoresuscitation induced by gasping. In rapid and strong inspiratory efforts during a gasp or a provoked aspiration reflex, activation of the inspiratory centre in the brainstem resets the failing centres of other vital functions, including the centres controlling cardiac activity, blood pressure, as well as various neuropsychic and somato-motor functions.

As indicated in PCT/NL2006/000599, without wishing to be bound by any theory, it is believed that inducing the aspiration reflex may be helpful in relation to the following 5 groups of disorders of the human body.

1. In patients with apnoea and hypopnoea caused by transient inactivity of the inspiratory neurons in the brainstem, induction of the aspiration reflex can reverse the apnoea or hypopnoea and restore spontaneous breathing. In patients with obstructive apnoea, the stimulation of the inspiratory centre in the brainstem may reverse the closure of the airways and restore normal breathing.
2. In patients with Transient Ischemic Attack (TIA), syncope, hypotension, migraine and hemorrhagic shock the aspiration reflex activates, via the respiratory centre, the brainstem vasomotor centre to evoke peripheral vasoconstriction and vasodilatation in the brain and heart, resulting in increase of blood pressure and consequently increased brain and heart perfusion, interrupting, terminating or at least alleviating the pathological condition.
3. Bronchospasm, laryngospasm, hiccup, epileptic seizures, and tremor in Parkinson's disease may be inhibited by impulses from the inspiratory centre via the reticular formation, transmitted through interneurons providing inhibitory influence to the relevant control centres in the brainstem and elsewhere.
4. In alternating hemiplegia, sleep paralysis and absence type epilepsy: stimulation via the inspiratory centre and interneurons activates the descending part of the reticular formation, which activates motoneurons, terminating, or at least alleviating the attack.
5, . In comatose states, depression, insomnia, Alzheimers disease, anorexia nervosa, bulimia, and autism, stimulation via the inspiratory centre and interneurons influences the ascending part of the reticular formation. This inhibits or provides relief in depression, bulimia, anorexia nervosa and increases concentration and other cognitive functions. This improves some comatose states, may inhibit the development of Alzheimer's disease and autism and has a positive influence on insomnia and psychiatric disorders.

Resuscitating stimulation of the inspiratory neurons of the brainstem should be understood to mean stimulation of the human body such that the aspiration reflex or its alternatives are induced, which will influence various brainstem centres. Through such stimulation other parts of the brain relevant for the conditions treatable with the device are influenced. The aspiration reflex and its alternatives have, as a common feature, strong and short inspiratory efforts comparable to that occurring before or during one or more of gasp, sniff, sigh or augmented breath.

Figure 1:
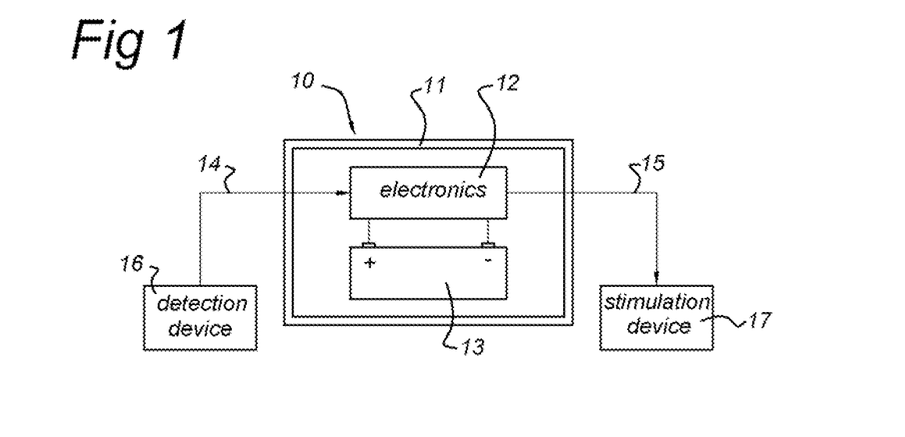
FIG. 1 shows a schematic block diagram of an electronic system according to the invention.

FIG. 1 shows a block diagram of a resuscitating device 10. The resuscitating device 10 has a casing 11. Enclosed in the casing 11 is a battery 13 which is connected to electronics 12. The battery 13 may comprise lithium iodine with nanocrystaline cathode components, as generally used in cardiac pacemakers. The electronics 12 are connected to a detection device 16 via suitable wires 14, as well as to a stimulation device 17 via suitable wires 15.

Figure 2:
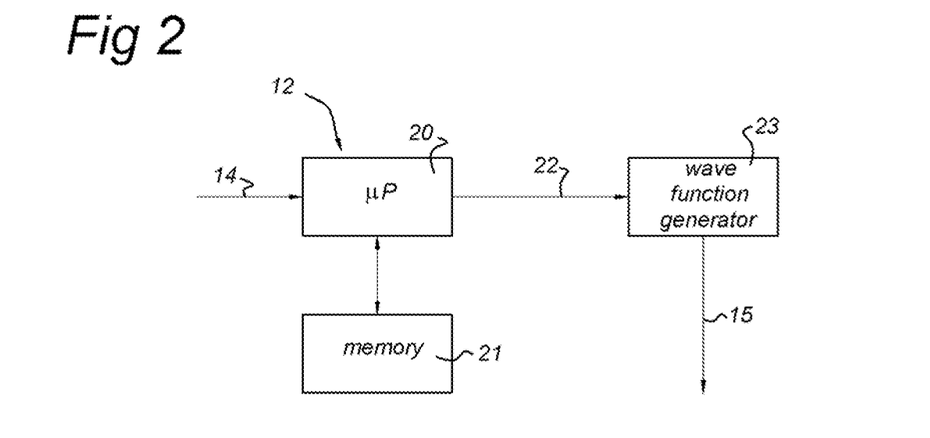
FIG. 2 shows an example of electronics that can be used in the present invention.

The electronics 12 may be implemented by means of an analogue circuit, a digital circuit or a computer arrangement with a processor instructed by a suitable computer program, or any combination thereof. FIG. 2 shows an embodiment based on a computer arrangement.

As shown in FIG. 2, the electronics 12 comprise a controller, e.g., in the form of a microprocessor 20 which is connected to a memory 21. Moreover, the microprocessor 20 is connected to a wave function generator 23 via suitable wires 22, which has an output connected to the wires 15 that are connectable to stimulation device 17.

The memory 21 may be implemented as several memory units of different types (RAM, ROM, etc.). The memory 21 stores instructions of a program to allow the microprocessor 20 to perform one or more functions. Optionally, memory 21 stores a number of detected parameter values as obtained from detection device 16. The memory 21 may be any suitable memory for storing a predetermined function such as a computer readable memory. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. E.g. the function may relate the absence of certain parameter values below a certain threshold value to a certain time frame. Such a function may be determined to detect the absence of breathing during a certain time period e.g. 2 seconds and longer, 5 seconds and longer or 10 seconds and longer.

Based on the program as stored in the memory 21, the microprocessor 20 is able to process the number of detected parameter values as obtained from the detection device 16 in said function. For this, the detected parameter values are loaded into the microprocessor 20 either directly from the detection device 16 or alternatively from the memory 21 into which the detected parameter values were previously loaded. The function is loaded in the microprocessor 20 from the memory 21 or in an alternative embodiment the predetermined function may be embedded in said microprocessor 20. In the latter embodiment at least one memory is (partially) integrated in the microprocessor 20.

The detection device 16 may be any suitable device for detecting a number of parameter values. In the present specification, a "number" shall mean one or more unless explicitly stated otherwise. In use, the detection device 16 provides an output signal on wire 14, representing determined parameter values in response to determined parameter values. The determined parameter values are values of a parameter as measured/determined by the detection device 16 within a certain time frame. The parameter may be any parameter on the basis of which it may be determined whether a subject is in need of induction of autoresuscitation.

Parameters suitable for determining whether a subject is in need of resuscitation include but are not limited to parameters corresponding to muscle activity, parameters corresponding to breathing, or parameters corresponding to cerebral activity, such as electrical activity of neural cells including brain cells, or electrical activity recorded from the pharynx, the ear or any other suitable point on the body of a human being.

Other sensors may be applied as well, like a sensor to measure body temperature, a sensor to measure pressure, and a sound sensor, like a microphone.

Parameters corresponding to muscle activity include but are not limited to movement and electrical activity of muscles. Movement of muscles may be detected by any detection device 16 suitable for detecting movement, such as a number of accelerometers. Electrical activity of muscles may be detected by use of any suitable device known in the art such as devices conventionally used for detecting an electromyogram (EMG), including an electrocardiogram (ECG), electroneurogram (ENG), actogram indicating contraction, etc. In one embodiment, the detection device 16 is arranged to record an electromyogram (EMG) detected by a detection electrode connected to the detection device 16. The detection electrode 16 may be suitable for attachment to the human diaphragm. The EMG data, including for instance intensity, frequency, repeatability of phasic activity, is processed in microprocessor 20.

Parameters corresponding to breathing, include but are not limited to parameters corresponding to activity of muscles involved in breathing activity such as the diaphragm, the intercostal muscles, musculus pectoralis, abdominal muscles, muscles of the upper and lower airways and other muscles involved. The parameters corresponding to muscle activity as discussed above are suitable. In an alternative embodiment of the device according to the invention, the parameter corresponding to breathing activity may comprise gas flow in the airways and/or in the vicinity of the inlets/outlets of the subject's airways. It must be understood that the inlets/outlets of the subject's airways comprise normally the nostrils and/or mouth or a tracheal tube in some patients. The skilled person will be familiar with suitable devices for determining gas flow, e.g. by a pneumotachograph or thermometer, such as a thermistor, Pt100, Pt1000 and other.

In a further alternative embodiment of the device 16, the parameters corresponding to breathing activity to be detected may comprise sound. During breathing sounds are created, for instance caused by air whirling in the larynx. Respiratory sounds include but are not limited to snoring, inspiratory and expiratory stridor, groaning, etc. These sounds may be used to detect breathing activity of a human being. Suitable detecting devices 16 for detecting sounds are microphones, a membrane connected to a coil/magnet system or any other device comprising a membrane with the possibility to register movement or displacement of this membrane. Such sounds may be detected in, for instance, at least one of the mouth, a nostril and an ear.

In a further alternative embodiment of the invention an electro encephalogram may be used by electronics 12. If so, detection device 16 is also arranged to detect electrical activity of the brainstem. Cerebral activity produces electrical fields which can be measured e.g. on the skin of the skull or the ear of a human being. Alternatively such signals may be recorded from the pharynx of a human being. Suitable devices for detecting electrical activity from the surface of the pharynx are conductive patches connected to a suitable amplifier and filter. The skilled person will be familiar with suitable devices for determining electrical activity of the brain from the skin.

Alternatively, the detection device 16 is connected to a sensor to measure oxygen saturation in the blood of the subject. This can be done in any way known to a person skilled in the art. Measuring oxygen saturation is a good indication of whether or not apnoea is present. In the embodiment of the invention this can advantageously be done in the ear itself, for instance, at the earlobe.

The stimulation device 17 is arranged to provide a response as a function of the number of processed parameter values. The stimulation device may comprise a number of stimulation units designed to provide resuscitating stimulation in order to stimulate and/or reactivate the inspiratory centre of the brainstem.

In accordance with the present invention an ear stimulator is used for resuscitating stimulation of the inspiratory centre of the brainstem. The ear stimulator is arranged to provide stimuli to one or more points on or in the ear, for instance on the auricle and/or auditory duct of the ear. The points are chosen such as to induce an aspiration reflex by the stimulation signal produced by the stimulation device 17.

The stimulation device 17 may be a mechanical or an electrical stimulation device. The electrical stimulation device may include a separate power source. A suitable power source may be an array of charged capacitors, allowing voltage selection for the stimulation, in case spikes are used. This separate power source may, alternatively, be absent in which case the stimulation device 17 will be connected to the battery 13 within casing 11 via wiring 15. The wave generator 23 as shown in figure 2 may be part of the stimulation device 17. In combination with such a power source, the wave generator 23 is arranged to produce a desired control signal for the stimulation device 17, for instance in the form of block waves, sinus waves or spikes of different length, frequency and amplitude, or combinations thereof.

The stimulation device 17 may further include or be connected to one or more stimulation electrodes for delivering an electrical stimulation to one or more acupuncture points of the ear. Such electrodes receive suitable stimulation signals based on the control signal received from the electronics 12. Electrodes may be mono-polar or multipolar, including bipolar electrodes, and may be placed on the surface of the body or anchored in various tissues of the subject's body. For stimulation of points on the ear, for instance the auricle of the ear, the electrodes may be placed on the skin. Between the electrode and the skin, a conducting gel or paste may be used. Alternatively electrodes may have the form of needles arranged to at least partially penetrate the subject's skin.

In an embodiment, the stimulation device 17 comprises a plurality of stimulation electrodes. By using a plurality of stimulation electrodes more complex stimulation currents can be provided to the body. This also provides the possibility of precise definition of the area to be stimulated. If a plurality of stimulation electrodes is used it is preferred that there is some distance between said electrodes. Due to this distance the electrical current will travel over that distance through the subject's body. This will enhance the stimulatory effect. It also allows to let the device auto-optimise the stimulation position, by optimising the effect as measured by the detection devices.

If spikes are used for the control signal, variations in the amplitude and duration of the spikes, i.e. the amount of energy can be made, apart from trains of spikes over an extended period of time (seconds) (Beňačka and Tomori, 1995). Sinus waves of various frequencies and duration, block waves, spikes, spike trains and any combination of these can be used. It is preferred to not just transfer energy, but to stimulate the targeted response centres more complexly to elicit the desired physiological response.

In an embodiment, the microprocessor 20 is designed to activate the wave function generator 23 if an EMG as detected by detection device 16 does not satisfy a predetermined criterion, such as a lack of normal EMG activity for >10 sec (central apnoea) or extremely strong EMG activity accompanied by stop of airflow (obstructive apnoea) as detected by detection device 16. Then, upon activation the wave function generator 23 may generate the control signal in the form of a predetermined wave, such as a sinus wave, block wave, spike train or any combination in a suitable frequency, duration and amplitude that is guided through electrical wires to its stimulation electrode.

Ear Stimulator

Figure 3A:
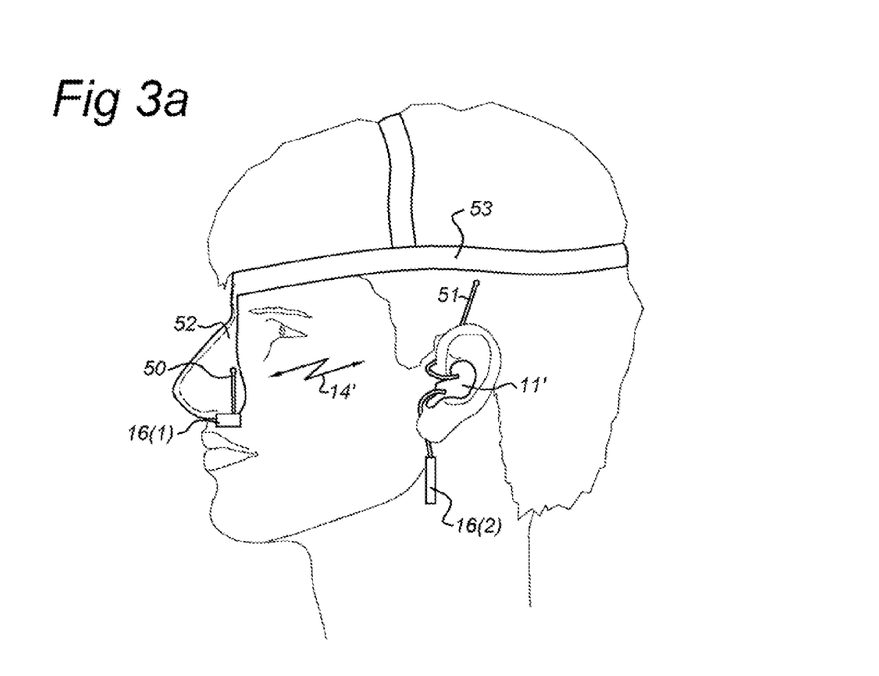
FIG. 3a shows a human head wearing a device according to an embodiment of the invention.

FIG. 3*a* shows an embodiment of an ear stimulator in accordance with the invention.

The ear stimulator as shown comprises two parts. The first part comprises a nose cap 52 that may be connected to one or more bands 53 that can be worn by a human head. Other supporting devices, like a hat or cap, can be used instead to fix the nose cap to the human nose and prevent the nose cap from falling of the head. The nose cap comprises a first detection device 16(1) which, in use, is located close to one or both of the nostrils and is arranged to sense airflow. Such an airflow sensor can be based on measuring temperature changes (e.g. via a thermistor), pressure changes, changes in airflow, etc. Thus, detection device 16(1) is arranged to sense whether or not the human being is still breathing. The detection device 16(1) generates a breathing signal in dependence on the sensed airflow and sends the breathing signal to the second part of the ear stimulator. Transmission of this breathing signal can be done via an antenna 50 and a wireless connection 14' as shown. However, a wire connection can be used instead.

Alternatively, or additionally, the detection device 16 may be connected to a canula provided with a breathing sensor to sense breathing through the mouth.

Although the first detection device 16(1) is shown to be attachable to a human's nose by means of a nose cap the invention is not restricted to this embodiment. Any holding device arranged to attach the first detection device 16(1) to the nose may be used instead, including a nose plug, a piercing, screws, nails, bolts, a click system, rivets, staples and bayonets. Such a holding device can be attached to one of the nostrils or the nose bone or any other suitable part of the nose.

The second part comprises casing 11' arranged to be inserted in an ear. Alternatively, the casing 11' can be made as an arrangement to be worn behind the human ear, e.g., like the P-STIM® device of E. Biegler GmbH (Austria).

Casing 11' is connected to an antenna 51 for receiving the signal as transmitted by antenna 50. Casing 11' may also be connected to a second detection device 16(2) which is arranged to sense a heart beat signal. In the shown embodiment, the second detection device 16(2) is arranged to be fixed to the human skin close to the carotid in order to sense the heartbeat from the blood flow in the carotid. However, alternatively, the second detection device 16(2) is arranged to be fixed inside the human ear and to sense noise inside the human ear. As a further alternative, second detection device 16(2) can be located on any portion of the human body where the heartbeat can be sensed, as explained above.

If detection device 16(2) is arranged to be located inside the ear, the second detection device 16(2) is arranged to transmit a heartbeat signal in the form of a noise signal to the electronics 12' inside casing 11'. Based on a suitable software program stored in memory 21, processor 20 can then generate a cardiogram based on the received noise signal as sensed inside the ear. Such a cardiogram is called an "audio cardiogram" and can be derived by using mathematical equations known to a person skilled in the art. Reference is, e.g., made to U.S. Pat. No. 6,988,993.

Alternatively, or additionally, a sound sensor like a microphone, can be located inside the ear which, in use, delivers a sound signal from which a breathing signal can be derived.

The processor 20, using a suitable program stored in memory 21, is arranged to determine whether the breathing signal as received from the first detection device 16(1) and the heartbeat signal received from the second detection device 16(2) indicate that the human being is suffering from apnoea. If so, the processor generates a suitable output signal for wave function generator 23 which, based on that output signal, will generate a suitable control signal for stimulation device 17.

The ear stimulator is arranged to stimulate one or more points on or in the ear, for instance on the auricle of the ear, that when stimulated induce an aspiration reflex. For stimulation of such points of the ear, for instance the auricle of the ear, the electrical stimulation device 17 may be designed such as in the P-STIM® device of E. Biegler GmbH (Austria). Such a device can be worn behind the ear.

Figure 4:
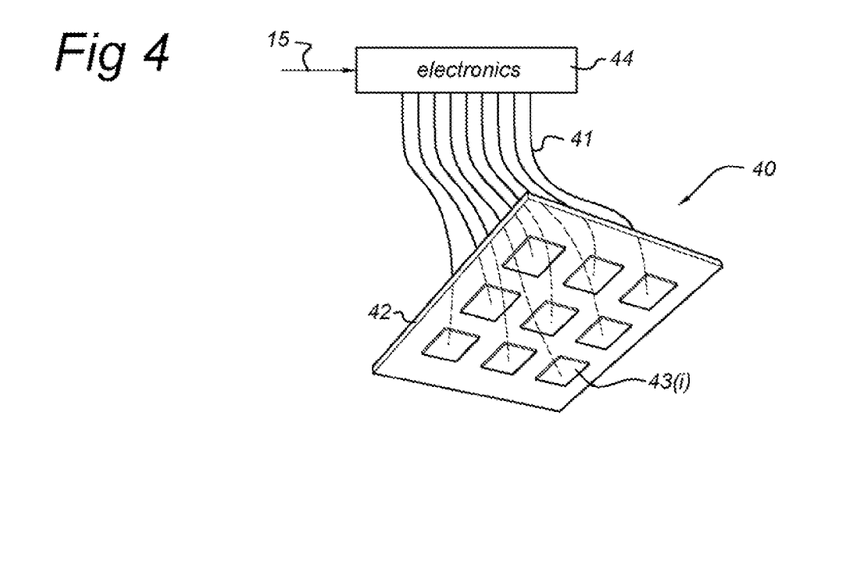
FIG. 4 shows a substrate with a matrix arrangement of stimulation units.

In an embodiment, the stimulation units 43($i$) are mechanical stimulation units arranged to provide a mechanical stimulus to the human body. Such mechanical stimulation units 43($i$) may be formed by electrostriction components which produce a mechanical movement when excited by an electrical current. Such mechanical stimulation units 43($i$) may have the form of needles.

In an alternative embodiment, the stimulation device 17 is a mechanical stimulation device arranged to mechanically stimulate points on the ear, for instance the auricle of the ear. Mechanical stimulation means are means that are suitable for touching with an elastic nylon fibre and thin polyvinyl catheter, or providing pressure to selected parts of the ear. Mechanical stimulation may be also provided by means of gas pressure pulses. Other suitable devices for providing mechanical pressure comprise acupuncture, acupressure, electro-acupuncture electro-acupressure (combination of mechanical and electrical stimulation) devices.

Figure 3B:
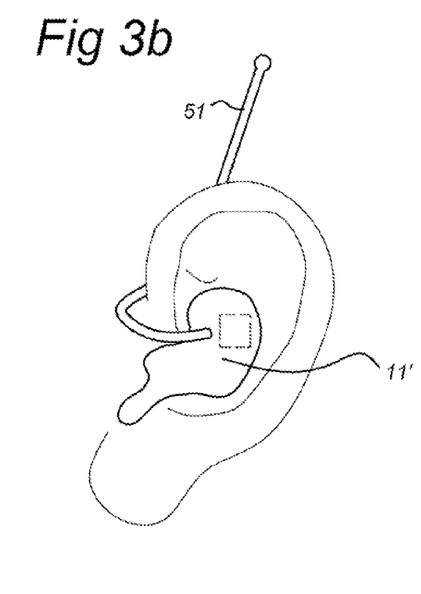
FIGS. 3b and 3c show ear pieces of embodiments of the invention in greater detail.

FIG. 3b shows a casing 11' like the one in FIG. 3a, however, at a larger scale. FIG. 3b shows that casing 11' comprises the stimulation device 17 which is shown in dashed lines. The casing 11' with stimulation device 17 is designed such that, when the ear piece is worn by a user in his/her ear the stimulation device 17 is pushed against the auricle of the ear such that it can provide the desired electrical and/or mechanical stimulus on the desired location. The casing 11' is connected to antenna 51 like in the embodiment of FIG. 3a.

Figure 3C:
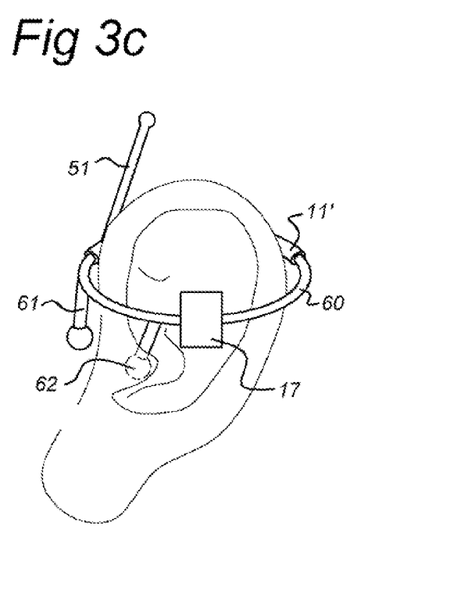

An arrangement that can be worn behind the ear is shown in the embodiment of FIG. 3c. The ear piece of the embodiment of FIG. 3c comprises a casing 11' that can be worn behind the ear. If desired, the casing 11' is connected to antenna 51 like in the embodiment of FIG. 3a. Stimulation device 17 is connected to casing 11' by means of a clamping unit 60, for instance in the form of a resilient rod, arranged such that, when the ear piece is worn by the user, the stimulation device 17 is pushed against the auricle of the ear such that it can provide the desired electrical and/or mechanical stimulus on the desired location.

In the embodiment of FIG. 3c, the ear piece is also connected to two separate microphones 61, 62 which are arranged such that, in use, one 62 of them is directed inside a human ear and the other one 61 of them is directed outside the human ear. Signals from both microphones 61, 62 will be provided to electronics 12 within casing 11'. Electronics 12 is arranged to use output signals received from the outwardly directed microphone 61 to filter background noise as present in the area surrounding the human being, from output signals received from the inwardly directed microphone 62 which may comprise a component due to this background noise. By doing so, electronics 12 can obtain a more pure signal relating to the noise inside the human ear only relating to noise produced by the human body and relating to breathing activity and/or heart beat. It is observed that such a double microphone arrangement can be applied in the other embodiments of the present invention as well. Moreover, the double microphone arrangement of FIG. 3c can be applied without the nose piece. If used without the nose piece, antenna 51 can be absent.

Although the embodiments of FIGS. 3a, 3b and 3c show stimulation on a part of the auricle facing away from the head, it is emphasized that the invention is not restricted to this embodiment. A stimulation may also be provided to a part of the auricle facing towards the head. Moreover, the stimulation may be provided to a part of the auditory duct.

In an embodiment, the ear stimulator comprises a stimulation matrix. FIG. 4 shows a stimulation matrix 40. The stimulation matrix 40 is part of or connected to the stimulation device 17. As shown in FIG. 4, the stimulation matrix 40 has a substrate 42 provided with a plurality of stimulation units 43($i$), $i=1, 2, 3, \ldots, I$. The stimulation units 43($i$) are arranged in a matrix form. The arrangement shown comprises stimulation units 43($i$) in a regular matrix pattern. However, the embodiment is not restricted to this arrangement. Irregular patterns may be used instead. In an embodiment the stimulation units 43($i$) are arranged in a two dimensional pattern.

In an embodiment, the stimulation units are stimulation electrodes 43($i$) for delivering an electrical stimulation to the human ear, e.g., to the auricle and/or auditory duct. Such electrodes 43($i$) receive suitable stimulation signals via wires 41 from electronics 44 within stimulation device 17 based on the control signal received from the electronics 12 via wire 15. Electrodes 43($i$) may be mono-polar or multipolar, including bipolar electrodes. For stimulation of acupuncture points on the ear, for instance the auricle of the ear, the electrodes 43($i$) may be placed on the skin. Alternatively, electrodes 43($i$) may have the form of needles arranged to at least partially penetrate the subject's skin.

By using a plurality of stimulation electrodes 43($i$) arranged in the form of a two dimensional matrix more complex stimulation currents can be provided to the ear. This also provides the possibility of precise definition of the area to be stimulated. There is some distance between the electrodes 43($i$). Due to this distance the electrical current will travel over that distance through the subject's ear. This will enhance the stimulatory effect. It also allows for auto-optimisation of the stimulation position, by optimising the effect as measured by the detection devices 16(1), 16(2).

If spikes are used for the control signal, variations in the amplitude and duration of the spikes, i.e. the amount of energy can be made, apart from trains of spikes over an extended period of time (seconds) (Beňačka and Tomori, 1995). Sinus waves of various frequencies and duration, block waves, spikes, spike trains and any combination of these can be used. It is preferred to not just transfer energy, but to stimulate the targeted response centres more complexly to elicit the desired physiological response.

Tests on several people have shown the following promising results. The stimulation device 17 was controlled by electronics 12 to provide a stimulation signal to a stimulation unit that converts the stimulation signal into either an electrical or mechanical stimulus (or both) of the form as shown in FIGS. 7a and 7b.

Figure 7A:
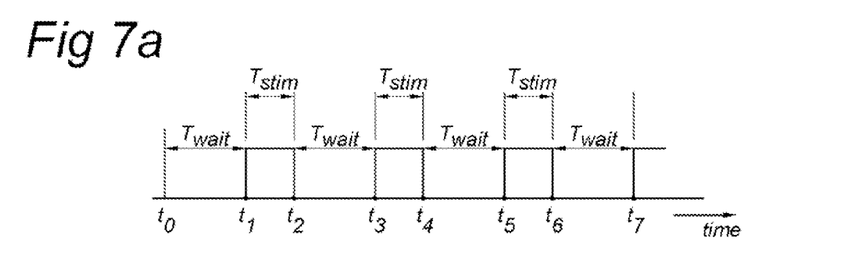
FIGS. 7a and 7b show examples of stimulation signals.
Figure 7B:
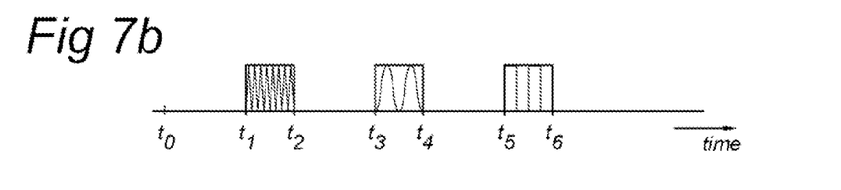

FIG. 7a shows a stimulation signal as generated by stimulation device 17 when the electronics 12 detect that a person is in a state of developing apnoea. At time $t_0$ electronics 12 determine that the person concerned was breathing such as to have a high risk of developing apnoea. The combination of electronics 12 and stimulation device 17 is arranged such that a first stimulation signal is only generated at a time $t_1$ after a first delay time $T_{wait}$. As shown in FIG. 7a, the first stimulation signal may have the form of a spike, pulse or wave train which lasts a predetermined time $T_{stim}$ until time $t_2$. If breathing has not started as a result of the first stimulus a second stimulation signal is generated at time $t_3$ after waiting time $T_{wait}$. Again, the stimulation signal lasts a time $T_{stim}$ until time $t_4$. A third second stimulation signal is generated at time $t_5$ after waiting time $T_{wait}$. Again, the stimulation signal lasts a time $T_{stim}$ until time $t_6$. Etc.

During the time the stimulation device 17 is generating the stimulation signal as shown in FIG. 7a, the electronics may, at any time interrupt the stimulation device 17 and cause stimulation device 17 to stop once the electronics 12 have determined that the person concerned has returned to breathing. The pattern shown in FIG. 7a may be generated by stimulation device 17 automatically once it has received a trigger signal from electronics 12 and may continue until it receives such an interrupt signal. Alternatively, electronics 12 may be arranged to control generating every stimulation pulse one-by-one.

In accordance with the present invention, the combination of electronics 12 and stimulation device 17 may be arranged to vary the waiting time $T_{wait}$ between consecutive stimulation pulses. It has been found that a suitable waiting time $T_{wait}$ may vary between 0 and 10 seconds, preferably between 0 and 5 seconds, more preferably between 0.5 and 2 seconds. Moreover, tests have shown that the stimulation time $T_{stim}$ may vary between 0 and 10 seconds, preferably between 0 and 5 seconds, more preferably between 0.5 and 2 seconds. Especially the first waiting time $T_{wait}$ may deviate from the other waiting times between consecutive stimulation pulses cf. for instance FIG. 9.

It is observed that the same tests have also shown that if a person does not continue breathing within 10 seconds after cessation of breathing but later, that applying the stimulation pattern leads to shortening the apnoea episodes.

It is observed that the same tests have also shown that if a person does not continue breathing within 10 seconds after cessation of breathing but later, that applying the stimulation pattern as shown in FIG. 7a results in the person having the feeling that he has been sleeping better then normally.

FIG. 7b shows that the actual stimulation signal within the pulse shaped pattern of FIG. 7a may have any desired form, i.e., a triangle form, a sinusoidal form, a block form, etc. Tests have shown that the average repetition frequency of the stimulation signal within the stimulation pulses may be between 1 and 500 Hz. Successful results as to counteracting apnoea have been shown with an average repetition frequency of about 8 and 60 Hz. A preferred range is therefore 1 to 100 Hz.

Figure 5:
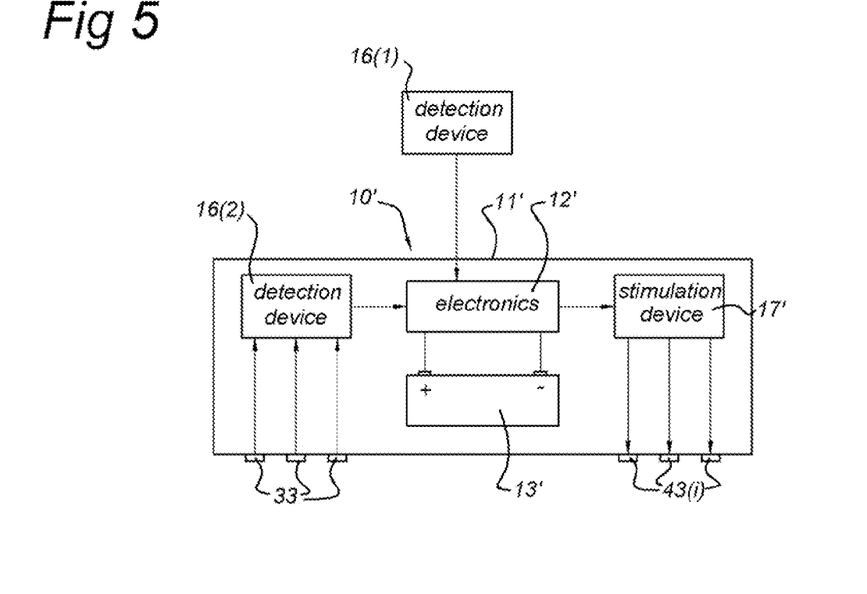
FIG. 5 shows an alternative arrangement of the arrangement of FIG. 1.

As observed above device 10 according to the invention may be designed such that it does not comprise any external detection or stimulation leads. As shown in FIG. 5, the casing 11' of such a device 10', then, accommodates all components including detection device 16(2), electronics 12', battery 13' and stimulation device 17'. The battery 13' is shown to be connected to the electronics 12' but may equally well be connected to the detection device 16(2) and the stimulation device 17'.

Then, the casing 11' may be partly conductive. For instance, the casing 11' may be provided with conductive pads 33 connected to the detection device 16(2) and operating as an antenna to detect electric activity of the human body e.g. for the detection of an EEG.

The conductive casing 11' may similarly be provided with the stimulation units 43(i) connected to the stimulation device 17' which are used to guide an electric stimulation current to the part of the human ear in its direct proximity.

In a further alternative embodiment, only the stimulation device 17' is located inside casing 11' and the stimulation units 43(i) are located on the casing 11' whereas detection circuit 16(2) is located outside casing 11' like in the arrangement shown in FIG. 1.

Casing 11' may be made from a conducting material like titan or platina. In such a case, when the stimulation units 43(i) themselves are conductive too they should be electrically isolated from the conductive casing 11'. This can be done in any way known to a person skilled in the art.

In one embodiment, the casing 11, 11' that accommodates electronics 12, 12' and battery 13, 13' is made of a flexible material. A suitable material is silicone since that is found to be well tolerated by the human body. However, other flexible biocompatible materials tolerated by the human body may be used instead.

The advantage of using a flexible casing 11, 11' is that it can well be used in, behind or on an ear: it adapts itself to the form of the ear. Thus, it does not, or hardly, perform any mechanical pressure to the ear, which would cause discomfort or even undesired stimulation by pressure.

Figure 6:
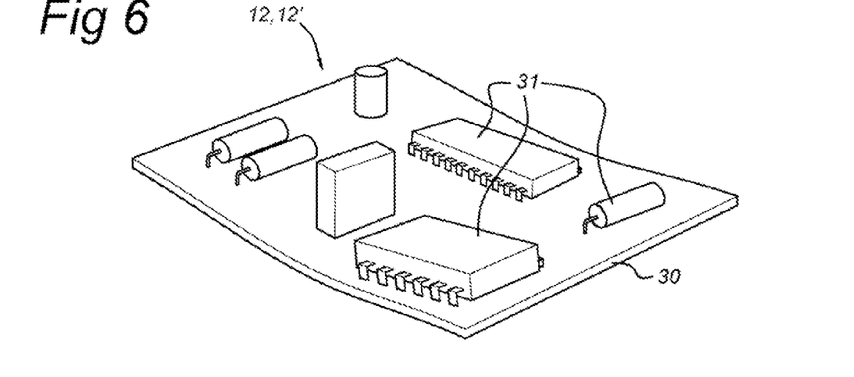
FIG. 6 shows a flexible substrate provided with electronic components.

In such an embodiment, the battery 13, 13' may be made flexible too. Alternatively, many small batteries may be joined to form a virtually flexible battery pack. The electronics 12, 12' may be made of flexible components as well or at least electronic components may be provided on a flexible substrate, e.g., a flexible printed circuit board. FIG. 6 shows such a flexible substrate 30 having electronic components 31 located on at least one surface. As shown in FIG. 5, the stimulation device 17' may be located inside the casing 11' too and be made of electronic components on a flexible substrate too. Then, the stimulation device 17' may be arranged as shown in FIG. 6 as well. The electronic components of the electronics 12' may be arranged on a first flexible substrate and the stimulation device 17' may be arranged on a second flexible substrate. However, these first and second substrates may be a single substrate. The battery 13' may be provided on that substrate too. As also shown in FIG. 5, the detection device 16(2) may be located inside the casing 11' too and be made of electronic components on a third flexible substrate too. Then, the detection device 16(2) may be arranged as shown in FIG. 6 as well. The substrates with the electronic components of the electronics 12', the detection device 16(2) and the stimulation device 17' may be separate substrates. Alternatively, however, they may be one single substrate.

Figure 8:
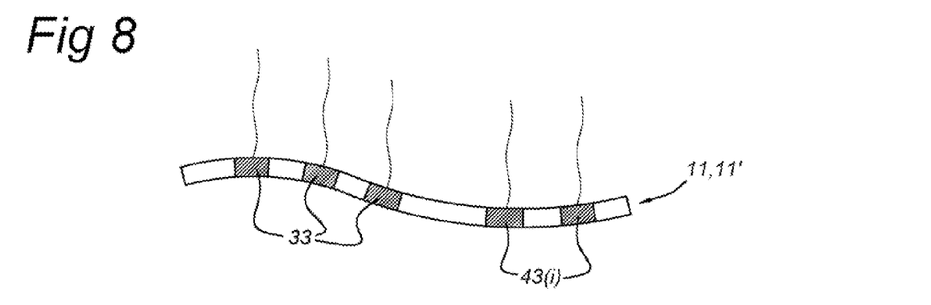
FIG. 8 shows a portion of a flexible casing with sensors and stimulation electrodes.

In the embodiment where the casing is made of silicone and the stimulation units are stimulation electrodes 43(i), these stimulation electrodes 43(i) can be made as electrically conductive silicone portions in the silicone casing 11'. This can be done by providing silicone portions of the casing 11' with doping materials like titan or platina. Such an embodiment is shown in FIG. 8. FIG. 8 shows a portion of a cross section of the flexible casing 11, 11' with sensors 33 and stimulation electrodes 43(i). In this embodiment, both the casing 11, 11' and the sensors 33 and the stimulations electrodes 43(i) are made of silicone. They are all produced from a silicone substrate in which predetermined portions are doped with a suitable doping material like titan or platina to become sensors 33 and stimulation electrodes 43(i). Suitable conductive wirings are connected to these latter portions for electrically connecting the sensors 33 to the detection device 16, 16' and the stimulation electrodes 43(i) to the stimulation device 17, 17'.

Such a device can be made auto-optimizing. The electronics 12, 12' can be arranged to perform a feedback measurement, such that stimulation can be performed at a point where the aspiration reflex can be elicited best. In one embodiment the electronics will, through a suitable sensor, register the strength of the aspiration reflex; this can for example be performed by measuring airflow through the nose or mouth, measuring sound, heart rate, blood pressure etc. Impedance of the stimulation point may be a guide for finding the optimal point. In this case the device may use impedance measurement to find suitable points for stimulation.

The electronics 12, 12' can be arranged to send different types of stimulation signals to the stimulation units 43(i), either in form or in amplitude or both. The effect of the different stimulation signals per stimulation unit 43(i) can be measured by detection devices 16(1), 16(2) and be evaluated by electronics 12, 12'. Electronics 12, 12' can be programmed to amend these stimulation signals by amending its control signal as output to the stimulation device 17, 17'.

Moreover, the electronics 12, 12' can be programmed to randomly vary its generated control signal such that the stimulation signals produce random stimuli over the area of the ear stimulated by the stimulation units 43(i). This could reduce adaptation of the body to the generated stimuli and, thus, enhance efficiency of the device 10, 10'.

The electronics 12, 12' can be programmed to evaluate the breath signal as received from the detection device 16(1) and to detect any breath disturbance, e.g., occurrence of hyperventilation. Then, based on this evaluation, electronics 12, 12' can produce a suitable control signal to the stimulation device 17, 17' such that the stimulation device 17, 17' produces suitable stimuli to the ear in order to counteract the breath disturbance.

Figure 9:
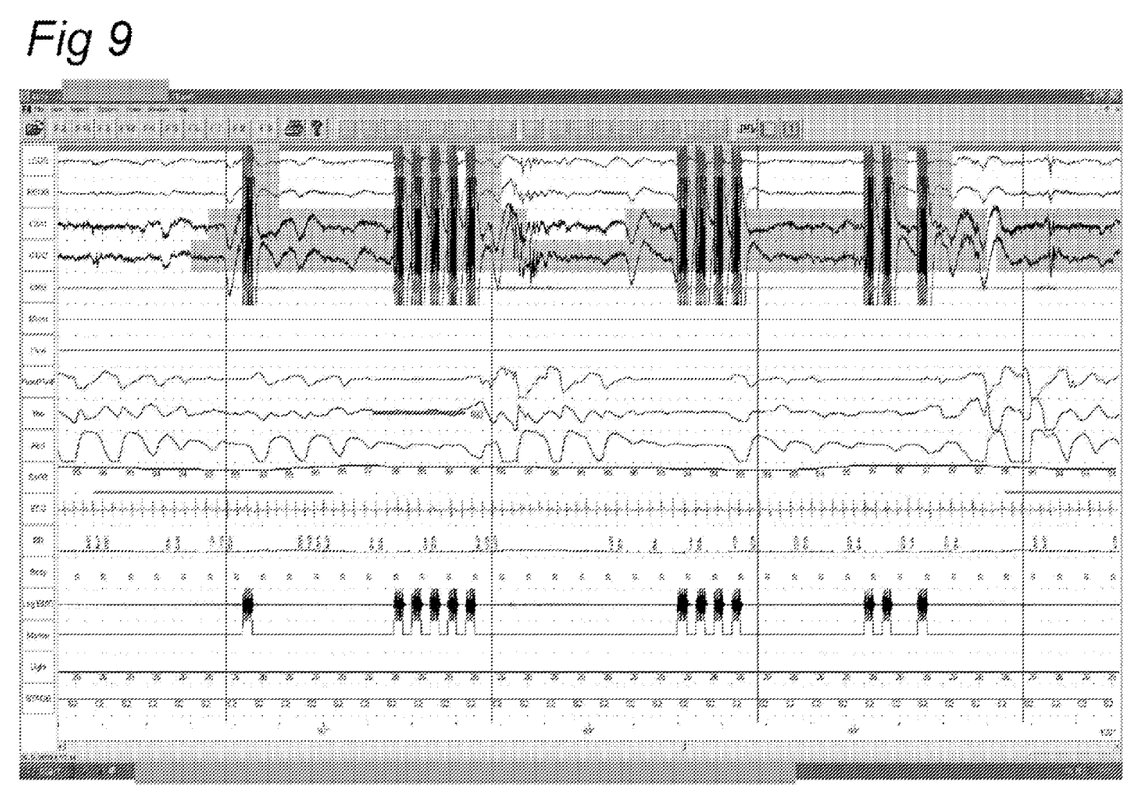
FIG. 9 shows some experimental results.

FIG. 9 shows some experimental results of providing stimulation to an auricle of a person suffering from sleep apnoea. The explanation to the parameters shown is as follows:

LEOG, REOG: Left and Right Electro OculoGram, respectively,
C3A1, C4A2: signals which are a measure of EEG,
EMG: Electro Myogram
FlowPTAF: breathing signal,
Tho: thorax movement
Abd: abdominal movement
SaO2: oxygen saturation
ECG: electrocardiogram
RR: heart rate
Leg EMG: Electro Myogram as measured on a leg
Marker: when high indicating a stimulation, when low indicating no stimulation FIG. 9 shows the following settings. 4 seconds after the apparatus has determined that the subject has stopped breathing or has started shallow breathing, the apparatus generated a stimulation signal to the auricle of the ear. The stimulation lasted 1 second. The stimulation signal itself had a frequency of 8 Hz. The time separating two consecutive stimuli was also 1 second. So, $t_1-t_0=4$ seconds, $t_{stim}=1$ second and $t_{wait}=1$ second.

In FIG. 9 the marker channel shows when a stimulation is addressed. As a consequence of this electric stimulation artefacts are shown in various electrically derived channels. In all cases breathing is resumed as a result of one or more stimulations, as is shown in the flowPTAF channel.

The method according to the invention is suitable for the treatment of one or more of but not limited to apnoea, such as central apnoea, obstructive apnoea or mixed type apnoea, transient ischemic attacks (TIA), hypotension, syncope, haemorhagic shock (loss of blood), bronchospasm, laryngospasm, hiccup, tremor associated with Parkinson's disease, epileptic seizure, absence type epilepsy, migraine, alternating hemiplegia, Alzheimers disease, depression, anorexia nervosa, bulimia, autism, psychiatric disorders, insomnia, sleep paralysis, comatose states. As used in this specification the term treatment should be construed to encompass alleviation of discomfort or provide reversal of life threatening functional disorders.

It should be understood that the embodiments presented in the examples above are solely intended to illustrate the present invention and are not intended to limit the scope of the invention which is only limited by the annexed claims and its technical equivalents.

References

Arita H., Oshima T., Kita I., Sakamoto M.: Generation of hiccup by electrical stimulation in medulla of cats. Neurosci. Lett. 175: 67-70, 1994.

Batsel H. L., Lines A. J.: Bulbar respiratory neurons participating in the sniff reflex in the cat, J. Exper. Neurol 39:469-481, 1973.

R. Beňačka, Disorders of central regulation of breathing and their influencing by upper airway reflexes (in Slovak). Orbis Medince S; No.: 53-63, 2004, R. Beňačka and Z. Tomori, The sniff-like aspiration reflex evoked by electrical stimulation of the nasopharynx, Respir. Physiol. 102: 163-174, 1995.

J. Jakuš, Z. Tomori and A. Stransky, Neural determinants of breathing, coughing and related motor behaviours, Monograph, Wist, Martin, 2004.

Sridhar R., Thach B. T. et al.: Characterization of successful and failed autoresuscitation in human infants including those dying of SIDS. Pediatr. Pulmon. 6:113-122, 2003.

St John W. M., Bledsoe T. A., Sokol H. W: Identification of medullary loci critical for neurogenesis of gasping J. Appl. Physiol. 56: 1008-1019, 1984.

Z. Tomori, M. Kurpas, V. Doni. and R. BeÁa.ka, Reflex reversal of apnoeic episodes by electrical stimulation of upper airway in cats, Respir. Physiol. 102: 175-185, 1995.

Z. Tomori, R. Beňačka, V. Doni. and J. Jakuš, Contribution of upper airway reflexes to apnoea reversal, arousal, and resuscitation, Monaldi Arch. Chest Dis. 55: 398-403, 2000.

Z. Tomori, R. Beňačka and V. Doni., Mechanisms and clinicophysiological implications of the sniff- and gasp-like aspiration reflex, Respir. Physiol. 114: 83-98, 1998.

Z. Tomori and J. G. Widdicombe, Muscular, bronchomotor and cardiovascular reflexes elicited by mechanical stimulation of the respiratory tract, J. Physiol 200: 25-49, 1969.

Xie J., Weil M. H., Sun S., Yu T., Yang W.: Spontaneous gasping generates cardiac output during cardiac arrest, Crit. Care Med. 32: 238-240, 2004.

The invention claimed is:

1. An electronic stimulation system arranged to be worn in, behind or on a human ear comprising
  a casing;
  a first detection device arranged to sense at least breathing activity from a human being and to generate a detection signal accordingly;
  electronics arranged within said casing and comprising a controller connected to said detection device and arranged to process said detection signal and to generate a control signal when said controller has determined that said human being is in a state of developing apnoea;
  a stimulation device arranged to receive said control signal from said electronics and to provide stimuli to one or more points of said human ear; and
  wherein said electronic stimulation system is arranged such that either said casing comprises said stimulation device and is arranged to be worn in said human ear such that when worn in the human ear, the stimulation device is pushed against an auricle of said human ear, or said casing is connected to said stimulation device by a clamping unit and is arranged to be worn behind the human ear such that when worn behind the human ear, the stimulation device is pushed against an auricle of said human ear, the stimulation device being arranged to generate a stimulation signal of a desired form with an average repetition frequency of 1 to 100 Hz during a plurality of stimulation times $T_{stim}$, a first stimulation time only starting after a first waiting time after said electronics have established that said human has a high risk of developing apnoea, consecutive stimulation times being separated by a second waiting time $T_{wait}$, a consecutive stimulation time starting after said second waiting time if the electronics have established that breathing has not started as a result of stimulation signals in a preceding stimulation time, wherein the first and further waiting time may be different, such as to provide an electrical stimulus to the auricle and provoke an induced aspiration reflex by a resuscitating stimulation of the respiratory area of the human brain stem, the first and second waiting time being between 0 and 10 seconds, and the stimulation time being between 0 and 10 seconds.

2. The electronic system according to claim 1, wherein the system comprises a second detection device arranged to sense a heartbeat of the human being, to generate a heartbeat signal to that effect and to transmit said heartbeat signal to said electronics, the electronics being arranged to generate said control signal also in dependence on said heartbeat signal.

3. The electronic system according to claim 2, wherein the system comprises a third detection device arranged to sense electrical signals from a brain of the human being and to generate an electro encephalogram (EEG) signal from the electrical signals, the electronics being arranged to generate said control signal also in dependence on said electro encephalogram signal.

4. The electronic stimulation system according to claim 1, wherein the detection device is fixed to a holding device arranged to attach the detection device to a human nose to allow said detection device to sense airflow caused by breathing through at least one of the nose or a mouth.

5. The electronic stimulation system according to claim 4, wherein said holding device is at least one of a nose plug, nose cap, a piercing, a screw, a nail, a bolt, a click system, a rivet, a staple and a bayonet.

6. The electronic stimulation system according to claim 5, wherein the holding device is a nose cap fixed to a supporting structure allowing said nose cap to be worn by the human being.

7. The electronic stimulation system according to claim 1, wherein said first detection device and said electronics are arranged to communicate with one another either via a wired connection or wirelessly.

8. The electronic stimulation system according to claim 2, wherein said second detection device is arranged to sense the heartbeat in at least one of a human carotid and another artery.

9. The electronic stimulation system according to claim 2, wherein said second detection device is arranged to generate the heartbeat signal from noise sensed within the human ear and thus to allow said electronics to generate an audio cardiogram.

10. The electronic stimulation system according to claim 1, wherein said system comprises two microphones arranged such that, when the system is worn in or on the human ear one of said microphones is directed inward to said human ear and another one of said microphones is directed outward from said human ear.

11. The electronic stimulation system according to claim 1, wherein the stimulation device is arranged to generate a plurality of stimulation signals during a stimulation time divided by a waiting time.

12. The electronic system according to claim 11, wherein the plurality of stimulation signals each have a form of one of a plurality of pulses, a plurality of triangular signals, a plurality of sinusoidal signals, a plurality of block signals.

13. The electronic system according to claim 11, wherein at least one of the waiting time and stimulation time is variable.

14. The electronic system according to claim 11, wherein the waiting time is between 0 and 5 seconds.

15. The electronic system according to claim 11, wherein the stimulation time is between 0 and 5 seconds.

16. The electronic stimulation system according to claim 1, wherein said casing is made from a flexible material.

17. The electronic stimulation system according to claim 1, wherein the electronic stimulation system comprises a plurality of stimulation units arranged in a two dimensional matrix form.

18. The electronic stimulation system according to claim 1, wherein said stimulation system is arranged as an auto-optimizing system.

19. The electronic stimulation system according to claim 18, wherein said stimulation system is arranged to identify a best location to provide a stimulus based on feedback signals from the detection device.

20. The electronic stimulation system according to claim 17, wherein the stimulation units are arranged as at least one of electrical stimulation units and mechanical stimulation units.

21. The electronic system according to claim 1, wherein the system comprises a sensor to measure oxygen saturation in blood of a subject at the ear.

22. A method of providing stimuli to a human ear comprising
  detecting at least breathing activity from a human being and generating a detection signal accordingly,
  processing said detection signal and generating a control signal when said human being is in a state of developing apnoea;
  receiving said control signal and providing stimuli to an auricle of said human ear;
  providing said stimuli to a predetermined portion of said human ear; and
  wherein the providing of the stimuli uses an electronic stimulation system arranged such that either a casing comprises a stimulation device and is arranged to be worn in said human ear such that when worn in the human ear, the stimulation device is pushed against an auricle of said human ear or said casing is connected to said stimulation device by a clamping unit and is arranged to be worn behind the human ear such that when worn behind the human ear , the stimulation device is pushed against an auricle of said human ear, the stimulation device being arranged to generate a stimulation signal of a desired form with an average repetition frequency of 1 to 100 Hz during a plurality of stimulation times $T_{stim}$, a first stimulation time only starting after a first waiting time after the electronic stimulation system has established that said human has a high risk of developing apnoea, consecutive stimulation times being separated by a second waiting time $T_{wait}$, a consecutive stimulation time starting after said second waiting time if the electronic stimulation system has established that breathing has not started as a result of stimulation signals in a preceding stimulation time, wherein the first and further waiting time may be different, such as to provide an electrical stimulus to the auricle and provoke an induced aspiration reflex by a resuscitating stimulation of the respiratory area of the human brain stem, the first and second waiting time being between 0 and 10 seconds, preferably between 0 and 5 seconds, more preferably between 0.5 and 2 seconds, and the stimulation time being between 0 and 10 seconds, preferably between 0 and 5 seconds, more preferably between 0.5 and 2 seconds.

23. An electronic stimulation system according to claim 14, wherein the first and second waiting times are between 0.5 and 2 seconds.

24. An electronic stimulation system according to claim 15, wherein the stimulation time is between 0.5 and 2 seconds.

25. An electronic stimulation system according to claim 16, wherein said flexible material is silicone.

* * * * *